United States Patent [19]

Wong

[11] Patent Number: 4,579,850

[45] Date of Patent: Apr. 1, 1986

[54] HALOGENATED ESTERS OF PYRIDINE ALKANOLS AND THEIR AMINE SALTS AS INSECT REPELLENTS

[75] Inventor: Rayman Y. Wong, Richmond, Calif.

[73] Assignee: Stauffer Chemical Company, Westport, Conn.

[21] Appl. No.: 705,169

[22] Filed: Feb. 25, 1985

[51] Int. Cl.⁴ .................... A01N 43/40; C07D 213/55
[52] U.S. Cl. .................................. 514/277; 546/341; 546/342
[58] Field of Search ................ 514/357, 277; 546/341, 546/342

[56] References Cited

U.S. PATENT DOCUMENTS 4,184,040 1/1980 Noteisz et al. ...................... 546/342
4,357,336 11/1982 Wong ................................ 546/342
4,457,934 4/1984 Wong ................................ 546/342

FOREIGN PATENT DOCUMENTS 1125764 6/1982 Canada ................................ 546/342

OTHER PUBLICATIONS

Porai-Koshits, et al., Chemical Abstracts, 61:5603e (1964).
Mikhlina, et al., Chemical Abstracts, 53:12863i (1958).
Augustinsson et al, Acta. Chemica Scandinavica, vol. 18, pp. 1006–1012 (1964); Chem. Ab., 61:8270c (1964).

Primary Examiner—Richard A. Schwartz
Attorney, Agent, or Firm—Joel G. Ackerman

[57] ABSTRACT

Compounds having the formula

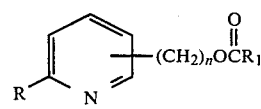

in which R is hydrogen or $C_1$–$C_4$ alkyl; $R_1$ is halo-($C_2$–$C_5$ alkyl); halo-($C_2$–$C_5$ alkenyl) or halo-(1-methylcyclopropyl); and n is an integer from 1 to 3, and their amine salts are insect repellents.

6 Claims, No Drawings

HALOGENATED ESTERS OF PYRIDINE ALKANOLS AND THEIR AMINE SALTS AS INSECT REPELLENTS

This invention relates to compounds having the formula

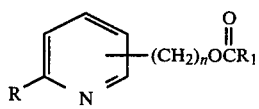

in which R is hydrogen or $C_1$–$C_4$ alkyl; $R_1$ is halo-($C_2$–$C_5$ alkyl); halo($C_2$–$C_5$ alkenyl) or halo-(1-methylcyclopropyl); and n is an integer from 1 to 3, and corresponding amine salts.

As will be shown from the data which follows, these compounds have been found to have utility in repelling insects, particularly repelling flying insects, and most particularly houseflies, from lighting and/or feeding.

In the compounds, the side chain may be attached to the pyridine ring at the 2-, 3- or 4-position. The term "halo" includes chloro, bromo, fluro and iodo and further includes both mono- and polyhalogenated (up to 3) groups of the types mentioned. Of the halogens, chloro and bromo are preferred. Most preferred for $R_1$ is haloalkenyl.

The amine salts of these compounds are also novel. Preferably the amine salts are amine hydrochlorides.

The esters of this type can be prepared by reaction of an appropriate pyridyl alkanol with an acyl halide (preferably chloride) according to the reaction

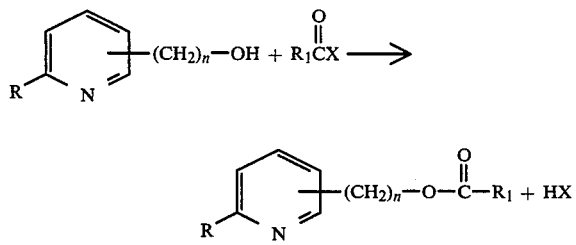

The pyridyl alkanols in which R is $C_1$–$C_4$ alkyl, if not commercially available, can be synthesized for example by the method of Umezawa et al., Japanese Patent Application No. 74/13180.

The reaction to produce the desired compounds is generally conducted at temperatures of from about −50° C. to about 25° C. in the presence of a solvent such as methylene chloride, or other suitable inert solvent and a hydrogen halide acceptor such as sodium bicarbonate, or a tertiary amine such as triethylamine or pyridine. The product is recovered by conventional extraction, washing, filtration, and other purification steps as may be necessary. Optionally, the hydrogen halide acceptor may be added after the reaction has gone to completion.

The preparation of these compounds is illustrated by the following example.

EXAMPLE 1

Preparation of 3-(3-Pyridyl)-1-propyl-2',3',3'-trichloroacrylate (Compound No. 1 herein)

In a flask were placed 5.0 grams (g) (0.036 mole) of 3-(3-pyridyl)-1-propanol, 3.2 g of pyridine and 50 milliliters (ml) methylene chloride. The clear yellow solution was cooled to −40° C. with an isopropanol ice bath; then there was added 7.8 g (0.040 mole) of trichloroacryloyl chloride (prepared in a previous step by hydrolysis of hexachloropropene in the presence of ferric chloride) at a rate so as to maintain the temperature of the mixture at 0° C. maximum. After addition was complete, the reaction mixture was warmed to room temperature and allowed to stir for one hour.

The mixture was washed with water, saturated aqueous sodium carbonate, water, and saturated aqueous sodium chloride, and dried over sodium sulfate. The dried solution was filtered through sodium sulfate and the solvent removed in vacuo to produce 8.0 g (82% of theoretical yield) of the desired product, a dark oil, which solidified on standing. The structure of the product was confirmed by infrared, nuclear magnetic resonance, and mass spectroscopy.

The following Table I contains a list of representative compounds of this invention which were prepared by the above process, and whose structure was similarly confirmed by analyses.

TABLE I

| Compound Number | R | $R_1$ | n | Position on Pyriding Ring | m.p. °C. or $n_D^{30}$ |
|---|---|---|---|---|---|
| Esters | | | | | |
| 1 | H | $-C(Cl)=CCl_2$ | 3 | 3— | dark oil |
| 2 | H | —(CH$_2$)$_3$Cl | 3 | 3— | 1.5040 |
| 3 | H | $-C(Br)=C(CH_3)_2$ | 3 | 3— | dark oil |
| 4 | H | —C(CH$_3$)$_2$CH$_2$Cl | 3 | 3— | 1.4970 |
| 5 | H | 1-methyl-2,2-dichlorocyclopropyl | 3 | 3— | 1.5175 |
| 6 | H | —C(CH$_3$)$_2$CH$_2$Cl | 1 | 3— | 1.5047 |
| 7 | H | —C(CH$_3$)$_2$CH$_2$Cl | 2 | 2— | 1.4984 |
| 8 | CH$_3$ | —C(CH$_3$)$_2$CH$_2$Cl | 3 | 2— | 1.4934 |
| Amine Hydrochlorides of Esters | | | | | |
| 9 | H | —CHBrCH$_2$Br | 3 | 3— | dark oil |
| 10 | H | —(CH$_2$)$_5$Br | 3 | 3— | 45–70° C. |

Insect Repellency Tests

The compounds described in Table I above were tested for insect repellency by the following procedures:

Houseflies

The insect utilized for this test was the housefly, *Musca domestica* (L.). One hundred houseflies of mixed sexes were placed in test cages. In each cage was placed a sugar cube saturated with 1.0 ml of acetone containing 0.1% by weight of the test compound. The cube was dried and weighed before being placed in the cage. Each cage also contained a water-saturated cotton plug to provide moisture. The test cages were placed on a turntable and rotated at 1.5 revolutions per minute to keep the flies randomly distrubuted inside the cage. After 48 hours the flies in each cage were anesthetized with carbon dioxide. The sugar cubes were removed and reweighed and the percentage weight loss (due to consumption by the flies) recorded. A repellency ratio, calculated at the percent weight loss of the treated sugar cube divided by the percent weight loss of a control sugar cube treated only with acetone and no test compound, was calculated. The lower the repellency ratio, the greater the repellency of the test compound. The repellency ratios of the test compound at different concentrations are shown in the following Table II.

Southern House Mosquitos

A cup filled with pupae of the mosquito *Culex pipiens quinquefasciatus* (Say) was placed in a screened cage and the puape allowed to emerge into adults. Sugar cubes were then saturated with 1.0 ml of an acetone solution containing 0.1 wt. % of the test compound, and, for a control, with the same amount of acetone alone. After the cubes dried they were put into the screened cage. Repellency was determined by the number of mosquito adults lighting and feeding on the sugar cubes, with observations being made daily for 5 days after treatment. The number of days of complete repellency of mosquitos from the sugar cubes was recorded and is reported in Table II under the heading "SHM"

Stable Fly; Yellow Fever Mosquito

Insects utilized for these tests were the stable fly, *Stomoxys calcitrans* and yellow fever mosquito, *Aedes aegypti*.

Pupae of these insects were placed in separate standard fly cages and allowed to to emerge into adults. The mosquitoes were supplied with a sugar-water solution; the stable flies with water, sugar cubes, and casein. Tests on mosquitoes were performed at least 3 days after the adults emerged; those on stable flies, one day after emergence because of the short life span (4–5 days) of these flies without a blood meal.

Test compounds were weighed and dissolved in acetone. One milliliter (ml) of the test solution was pipetted onto a 9×9 cm swatch of cotton stocking. The swatches were then allowed to dry for 1 hour.

A square opening 6×6 cm was made in an upper corner of one side of each fly cage. A large, hard cardboard disk was placed over the opening so that it could be rotated to either cover or expose the opening as desired. One-half of the disc was left intact. In the remaining half, several 6×6 cm square openings were cut. When the intact half of this disc was located over the opening in the fly cage, this opening was effectively sealed.

Swatches of treated stocking were placed over the square holes in the disc and held in place by metal frames attached to magnetic tape.

To initiate the test the disc was rotated so that a treated swatch became located over the opening in the cage. The palm of the tester's hand was placed over a cardboard ring, 8 cm in diameter and 1 cm thick. The ring acted as a spacer and protected the hand from bites which could otherwise be inflicted by the insects. A breath of air was exhaled through tubing into the opening, so that insects could be attracted to the swatch by the warm, moist air and the tester's hand. The number of insects landing on the swatch was observed, and the number probing, recorded during a 1-minute exposure. Repellency was considered to occur when 5 or fewer insects probed the swatch during the exposure.

The compounds were tested at the rate of 0.1 mg/cm$^2$ of swatch. Repellency is considered to be demonstrated if fewer than 10 insects per minute are observed probing. The results of these tests on stable flies (SF) and yellow fever mosquitoes (YFM) are contained in Table II.

TABLE II

| Compound Number | HF, Repellency Ratio | SHM, Days Repelled | Number of Insects Probing per minute | |
|---|---|---|---|---|
| | | | SF | YFM |
| 1 | 0.31 | 4.0 | >10 | >10 |
| 2 | 0.71 | >5 | — | — |
| 3 | 0.53 | >5 | >10 | >10 |
| 4 | 0.47 | 11 | >10 | >10 |
| 5 | 0.46 | >5 | >10 | >10 |
| 6 | 0.60 | >10 | >10 | 3 |
| 7 | 0.76 | — | >10 | 2 |
| 8 | 0.27 | — | >10 | >10 |
| 9 | 0.48 | — | >10 | >10 |
| 10 | 0.52 | — | >10 | >10 |

The novel compounds of this invention may be used as an insect repellent in either diluted or undiluted form. When used in a diluted form, compositions may contain relatively high or relatively low concentrations of the active compound. For example, the active compound can be incorporated into relatively high concentration compositions such as wet sprays or solutions in alcohol or other suitable solvents. Such compositions may contain, in addition to the active compound, adjuvants such as emulsifying agents, surface-active agents, anti-oxidants and propellants which may be normally found in insect repellent preparations. The active compound of this invention may be employed as the sole active component of such compositions or may be used in admixture with other compounds having a similar or different utility. For example, the compound may be incorporated into creams, lotions, powders, suntan oil, insecticides and other preparations which may contain pesticidal or other useful substances, as well as into compositions of various types used for treating fabrics or articles of clothing to render them insect repellent. In general, compositions for repellent use may contain from 0.1 up to 95 weight %, preferably from 1 to about 40 weight %, of the novel compound. High concentration formulations, containing up to 95% of the compound, could also be utilized for low-volume spraying from the air.

Examples of typical formulations employing the compound of this invention are for instance, Example 1: Emulsifiable Concentrate

| Component | Weight % |
|---|---|
| Compound 1 | 53.6 |
| Aromatic Hydrocarbon Solvent | 36.4 |
| Emulsifier | 10.0 |
| Total | 100.0 |

Example 2: Lotion

| Component | Weight % |
|---|---|
| Compound 2 | 10.7 |
| Lanolin | 4.8 |
| Mineral Oil | 8.0 |
| Trihydroxyethylamine stearate | 1.8 |
| Glycosterin | 0.8 |
| Glycerine | 4.6 |
| Sodium Benzoate | 1.0 |
| Water | 68.3 |
| Total | 100.0 |

Example 3: Alcohol Solution

| Component | Weight % |
|---|---|
| Compound 3 | 53.6 |
| Isopropanol | 46.4 |
| Total | 100.0 |

Example 4: Alcohol Solution

| Component | Weight % |
|---|---|
| Compound 4 | 80.0 |
| Ethanol | 20.0 |
| Total | 100.0 |

Example 5: Wettable Powder

| Component | Weight % |
|---|---|
| Compound 5 | 26.9 |
| Hydrated Calcium Silicate | 62.1 |
| Sodium Lignosulfonate | 5.0 |
| Orzan A (mixture of ammonium lignosulfonate and wood sugars) | 5.0 |
| Wetting Agent | 1.0 |
| Total | 100.0 |

What is claimed is:

1. A compound having the formula

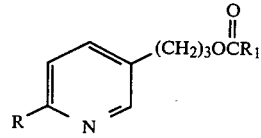

in which R is hydrogen or methyl; $R_1$ is selected from the group consisting of 1,2,-dichlorovinyl; 3-chloropropyl; 1-bromo-2-methyl-propen-1-yl; 1,1-dimethyl-2-chloroethyl; 1-methyl-2,2-dichlorocyclopropyl; 1,2-dibromoethyl; and 5-bromopentyl; or a hydrochloride acid addition salt thereof at the pyridine nitrogen atom.

2. A compound according to claim 1 in which R is hydrogen.

3. A hydrochloride acid addition salt according to claim 1 in which R is hydrogen.

4. An insect repelling composition containing an amount of a compound according to claim 1 effective to repel insects from a locus, and an inert diluent or carrier suitable for insect repellent compositions.

5. A method for repelling insects comprising applying to a locus to be protected from insects, an amount of a compound according to claim 1, effective to repel insects from said locus.

6. A method for repelling insects comprising applying to a locus to be protected from insects, an amount of a composition according to claim 4, effective to repel insects from said locus.

* * * * *